United States Patent
Kadobayashi et al.

(10) Patent No.: US 9,880,145 B2
(45) Date of Patent: Jan. 30, 2018

(54) SENSOR, PHASE SEPARATION DETECTING SYSTEM AND PHASE SEPARATION DETECTING METHOD

(71) Applicant: YAMAHA HATSUDOKI KABUSHIKI KAISHA, Iwata-shi, Shizuoka (JP)

(72) Inventors: Yoshiyuki Kadobayashi, Shizuoka (JP); Hiroyuki Matsumoto, Shizuoka (JP)

(73) Assignee: YAMAHA HATSUDOKI KABUSHIKI KAISHA, Shizuoka (JP)

(*) Notice: Subject to any disclaimer, the term of this patent is extended or adjusted under 35 U.S.C. 154(b) by 381 days.

(21) Appl. No.: 14/596,428

(22) Filed: Jan. 14, 2015

(65) Prior Publication Data
US 2016/0033469 A1  Feb. 4, 2016

(30) Foreign Application Priority Data
Aug. 1, 2014  (JP) .................................. 2014-157449

(51) Int. Cl.
*G01N 33/28* (2006.01)
(52) U.S. Cl.
CPC ................................ *G01N 33/2847* (2013.01)
(58) Field of Classification Search
CPC ................................................ G01N 33/2847
USPC ........................................................ 73/61.43
See application file for complete search history.

(56) References Cited

U.S. PATENT DOCUMENTS

| | | | | |
|---|---|---|---|---|
| 4,672,842 A | * | 6/1987 | Hasselmann | G01F 1/007 374/115 |
| 6,206,056 B1 | * | 3/2001 | Lagache | B67D 7/365 141/198 |
| 6,347,884 B1 | | 2/2002 | Faure et al. | |
| 6,578,416 B1 | * | 6/2003 | Vogel | G01F 23/265 73/290 R |
| 2006/0169039 A1 | * | 8/2006 | Zalenski | G01F 23/2963 73/290 R |
| 2007/0241849 A1 | * | 10/2007 | Heinrich | F16F 15/005 335/215 |
| 2012/0291530 A1 | * | 11/2012 | Aoki | G01N 33/2852 73/61.43 |

FOREIGN PATENT DOCUMENTS

| | | |
|---|---|---|
| JP | 61-040552 A | 2/1986 |
| JP | 61-128504 A | 6/1986 |
| JP | 03-082937 A | 4/1991 |
| JP | 2001-513199 A | 8/2001 |
| JP | 2007-262915 A | 10/2007 |
| JP | 2010-030623 A | 2/2010 |

* cited by examiner

*Primary Examiner* — Walter L Linsay, Jr.
*Assistant Examiner* — Philip Marcus T Fadul
(74) *Attorney, Agent, or Firm* — Keating and Bennett, LLP

(57) ABSTRACT

A sensor includes a detection portion and an output portion. The detection portion is made of a material that changes in accordance with a ratio of an actual amount of water to an amount of water causing a phase separation in an alcohol containing fuel. The output portion is configured or programmed to output a signal in accordance with a change of the detection portion.

28 Claims, 8 Drawing Sheets

ACTUAL AMOUNT OF WATER [vol%]

| | | ALCOHOL CONCENTRATION [vol%] | | | | | |
|---|---|---|---|---|---|---|---|
| | | 0 | 10 | 20 | 25 | 30 | 50 |
| PHASE SEPARATION WATER RATIO | 0 | 0 | 0 | 0 | 0 | 0 | 0 |
| | 0.5 | – | – | 0.25 | 0.65 | 0.9 | 1.2 | 2.35 |
| | 1 | – | – | 0.5 | 1.3 | 1.8 | 2.4 | 4.7 |

FIG. 3

SENSOR, PHASE SEPARATION DETECTING SYSTEM AND PHASE SEPARATION DETECTING METHOD

BACKGROUND OF THE INVENTION

1. Field of the Invention

The present invention relates to a sensor, a phase separation detecting system and a phase separation detecting method.

2. Description of the Related Art

Alcohol containing fuels absorb moisture in the air. Thus, the water concentration in alcohol containing fuels increases. A phenomenon called phase separation, meaning that gasoline and water are separated, is caused when the water concentration in the alcohol containing fuel reaches a predetermined concentration or greater. When phase separation is caused, alcohol is inevitably trapped into a water layer because of its highly hydrophilic properties. In this case, chances are that the octane number of the fuel or the vapor pressure decreases, and accordingly, the function of an engine or a fuel system degrades.

The amount of water that causes the phase separation varies in accordance with temperature and the alcohol concentration in the alcohol containing fuel. Further, the alcohol concentration in the alcohol containing fuel varies depending on regions. Thus, it is difficult to accurately detect a possibility of occurrence of the phase separation only by simply detecting the amount of water contained in the alcohol containing fuel.

In view of the above, a control device for alcohol blended fuel, described in Japan Laid-open Patent Application JP-A-2007-262915, is configured to calculate the amount of water containable in the fuel without causing the phase separation with use of an ethanol concentration sensor and an outdoor temperature sensor. Further, the possibility of occurrence of the phase separation is evaluated by comparing a calculated acceptable amount of water and an amount of water measured by a WIF (water-in-fuel) sensor.

The control device described in JP-A-2007-262915 at least requires the ethanol concentration sensor, the outdoor temperature sensor, and the WIF sensor in order to detect the possibility of occurrence of the phase separation. Thus, the control device includes the drawbacks of being structurally complicated and increasing the manufacturing cost.

It should be noted that Paragraph [0051] in JP-A-2007-262915 describes that the WIF sensor may not be provided if it is possible to estimate a boundary of occurrence of the phase separation (phase separation line) with a predetermined accuracy. However, the control device described in JP-A-2007-262915 cannot detect the amount of water contained in the alcohol containing fuel when it is not provided with the WIF sensor. Thus, the accuracy in detecting the possibility of occurrence of the phase separation remarkably degrades. Further, JP-A-2007-262915 discloses the condition "if it is possible to estimate a boundary of occurrence of the phase separation (phase separation line) with a predetermined accuracy". However, it is difficult to estimate the boundary in the first place.

On the other hand, when the water concentration in the alcohol containing fuel increases even though it is not high enough to cause the phase separation, some functional disorder could be caused by a change in shape of a fuel-based material due to swelling, corrosion, or formation of extraneous substances due to extraction. The amount of water, thus affecting such a function, is not an absolute amount but an amount relative to the amount of water causing the phase separation. Therefore, similarly to detecting the possibility of occurrence of the phase separation, it is difficult to accurately detect the possibility of occurrence of the above-described functional disorder only by simply detecting the amount of water contained in the alcohol containing fuel. Consequently, it has been demanded to accurately detect, with a simple structure, a ratio of an actual amount of water to the amount of water causing the phase separation in an alcohol containing fuel.

SUMMARY OF THE INVENTION

Preferred embodiments of the present invention provide a sensor that accurately detects a ratio of an actual amount of water to an amount of water causing the phase separation with a simple structure. Further, other preferred embodiments of the present invention provide a phase separation detecting system that accurately detects the possibility of occurrence of the phase separation with a simple structure. Yet further, other preferred embodiments of the present invention provide a phase separation detecting method that accurately detects the possibility of occurrence of the phase separation with a simple structure.

A sensor according to a first preferred embodiment of the present invention includes a detection portion and an output portion. The detection portion is made of a material that changes in accordance with a ratio of an actual amount of water to a boundary amount of water. The boundary amount of water is an amount of water that causes a phase separation in an alcohol containing fuel. The output portion is configured or programmed to output a signal in accordance with a change of the detection portion.

In the sensor according to the first preferred embodiment of the present invention, the detection portion changes in accordance with the ratio of the actual amount of water to the boundary amount of water when disposed in the alcohol containing fuel. The output portion is then configured or programmed to output a signal in accordance with the change of the detection portion. Thus, the ratio of the actual amount of water to the boundary amount of water is accurately detected. Further, the detection portion is made of the material that changes in accordance with the ratio of the actual amount of water to the boundary amount of water. The ratio of the actual amount of water to the boundary amount of water is detected by the change. Therefore, the sensor has a simple structure.

A phase separation detecting system according to a second preferred embodiment of the present invention detects a possibility of occurrence of a phase separation in an alcohol containing fuel, and includes a detection portion, a storage device, an output portion, and an evaluation portion. The detection portion is made of a material that changes in accordance with a ratio of an actual amount of water to a boundary amount of water. The boundary amount of water is an amount of water that causes the phase separation in the alcohol containing fuel. The storage device is configured or programmed to store a predetermined threshold. The output portion is configured or programmed to output a change value in accordance with a change of the detection portion. The evaluation portion is configured or programmed to evaluate the possibility of the occurrence of the phase separation based on the predetermined threshold and the change value.

In the phase separation detecting system according to the second preferred embodiment of the present invention, the detection portion changes in accordance with the ratio of the actual amount of water to the boundary amount of water when disposed in the alcohol containing fuel. The output portion is then configured or programmed to output the change value in accordance with the change of the detection portion. Further, the evaluation portion is configured or programmed to evaluate the possibility of occurrence of the phase separation based on the predetermined threshold and the change value. Thus, the possibility of occurrence of the phase separation is accurately detected. Further, the detection portion is made of the material that changes in accordance with the ratio of the actual amount of water to the boundary amount of water. The ratio of the actual amount of water to the boundary amount of water is detected by the change. Therefore, the phase separation detecting system has a simple structure.

A method according to a third preferred embodiment of the present invention is a phase separation detecting method of detecting a possibility of occurrence of a phase separation in an alcohol containing fuel. The method according to the third preferred embodiment of the present invention preferably includes the following steps. In the first step, the detection portion is provided. The detection portion is made of a material that changes in accordance with a ratio of an actual amount of water to a boundary amount of water. The boundary amount of water is an amount of water that causes the phase separation in the alcohol containing fuel. In the second step, a threshold is set. The threshold is determined based on the boundary amount of water. In the third step, a change value in accordance with a change of the detection portion is outputted. In the fourth step, the possibility of occurrence of the phase separation is evaluated based on the predetermined threshold and the change value.

In the phase separation detecting method according to the third preferred embodiment of the present invention, the detection portion changes in accordance with the ratio of the actual amount of water to the boundary amount of water when disposed in the alcohol containing fuel. The output portion is configured or programmed to output the change value in accordance with the change of the detection portion. The possibility of occurrence of the phase separation is then evaluated based on the predetermined threshold and the change value. Thus, the possibility of occurrence of the phase separation is accurately detected. Further, the detection portion is made of the material that changes in accordance with the ratio of the actual amount of water to the boundary amount of water. The ratio of the actual amount of water to the boundary amount of water is detected by the change. Therefore, the detection portion has a simple structure.

The above and other elements, features, steps, characteristics and advantages of the present invention will become more apparent from the following detailed description of the preferred embodiments with reference to the attached drawings.

BRIEF DESCRIPTION OF THE DRAWINGS

FIG. 3 is a table representing a relationship among an alcohol concentration, a phase separation water ratio, and an actual amount of water.

DETAILED DESCRIPTION OF THE PREFERRED EMBODIMENTS

Preferred embodiments of the present invention will be hereinafter explained with reference to the attached drawings. It should be noted that the following explanation is essentially illustrative only, and is not intended to limit the present invention, its application or its use.

Figure 1:
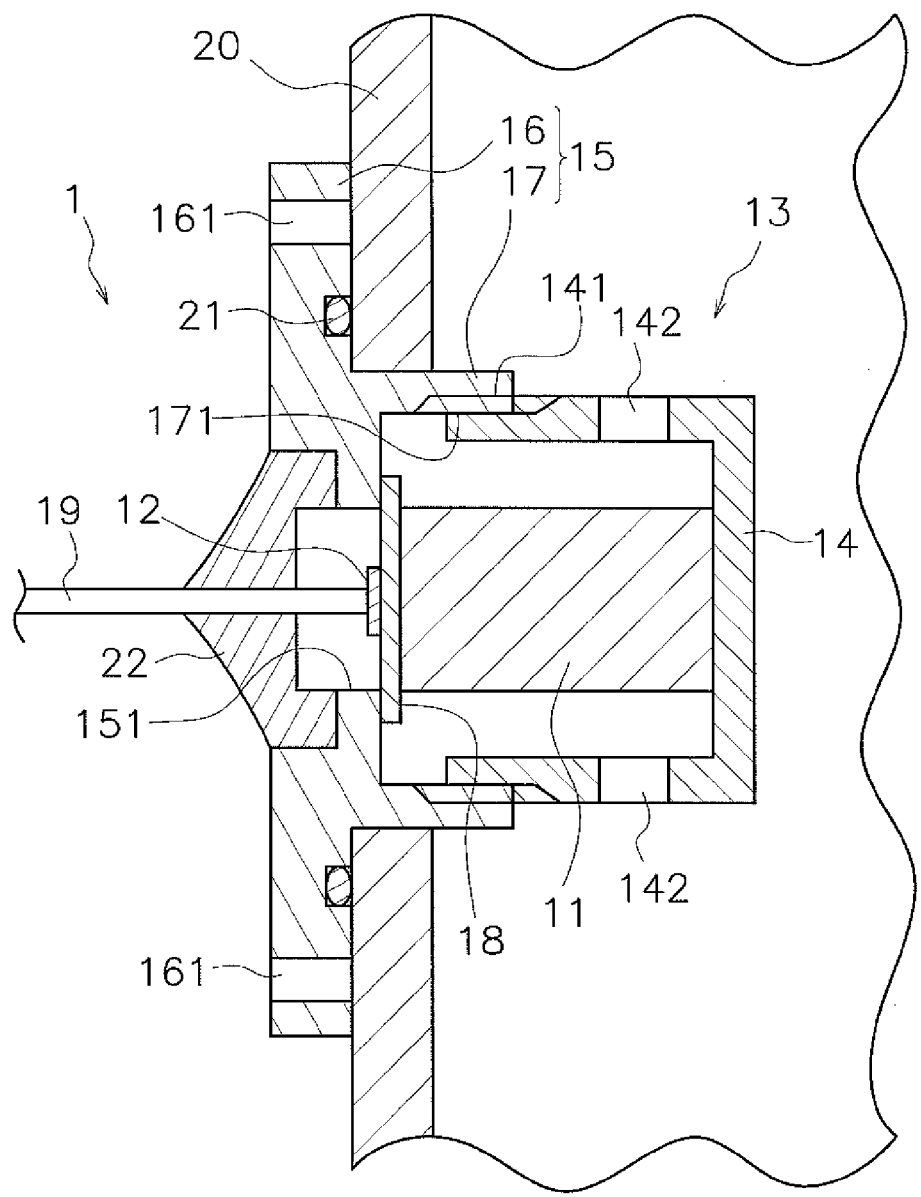
FIG. 1 is a schematic view of a sensor according to a preferred embodiment of the present invention.

FIG. 1 is a schematic diagram of a sensor 1 according to a first preferred embodiment of the present invention. The sensor 1 is attached to a fuel container 20 configured to store fuel. As shown in FIG. 1, the sensor 1 includes a detection portion 11 and an output portion 12. The detection portion 11 is made of a material that changes in accordance with a ratio of an actual amount of water to a boundary amount of water (hereinafter referred to as "a phase separation water ratio"). The boundary amount of water indicates an amount of water causing phase separation in an alcohol containing fuel. In the present preferred embodiment, the alcohol containing fuel indicates a gasoline fuel that contains ethanol, for example. However, the alcohol containing fuel may be of another type.

The sensor 1 includes a case 13. The case 13 includes a housing portion 14 and an attachment portion 15. The housing portion 14 accommodates the detection portion 11. The attachment portion 15 is attached to the fuel container 20. The attachment portion 15 includes a flange portion 16 and a tubular portion 17. The flange portion 16 includes attachment holes 161. The flange portion 16 is attached to the fuel container 20 by inserting screws, for example, (not shown in the drawings) through the attachment holes 161. A clearance produced between the flange portion 16 and the fuel container 20 is sealed by an O-ring 21.

The tubular portion 17 includes a female threaded portion 171 on the inner peripheral surface thereof. The housing portion 14 includes a male threaded portion 141 on the outer peripheral surface thereof. The housing portion 14 is attached to the attachment portion 15 by screwing the male threaded portion 141 of the housing portion 14 into the female threaded portion 171 of the tubular portion 17. A plate member 18 is disposed inside the tubular portion 17. The detection portion 11 is interposed and held between the plate member 18 and the housing portion 14. Thus, a compression preload is applied to the detection portion 11.

The housing portion 14 includes immersion apertures 142. The fuel stored in the fuel container 20 flows into the housing portion 14 through the immersion apertures 142. The attachment portion 15 includes a lead hole 151. The lead hole 151 is opposed to the plate member 18. The output portion 12 is attached to the plate member 18. A lead wire 19, connected to the output portion 12, is inserted through the lead hole 151. A clearance produced between the lead hole 151 and the lead wire 19 is sealed by a molding 22.

The detection portion 11 is made of a material that has swelling properties. A swelling ratio of the detection portion 11 varies in accordance with the phase separation water ratio. When described in detail, the swelling ratio of the detection portion 11 increases with an increase in the phase separation water ratio.

The detection portion 11 is preferably made of resin, for example. The detection portion 11 is more preferably made of polyamide-based resin, for example. In the present preferred embodiment, the detection portion 11 is preferably made of PA6 (nylon 6), for example.

Figure 2:
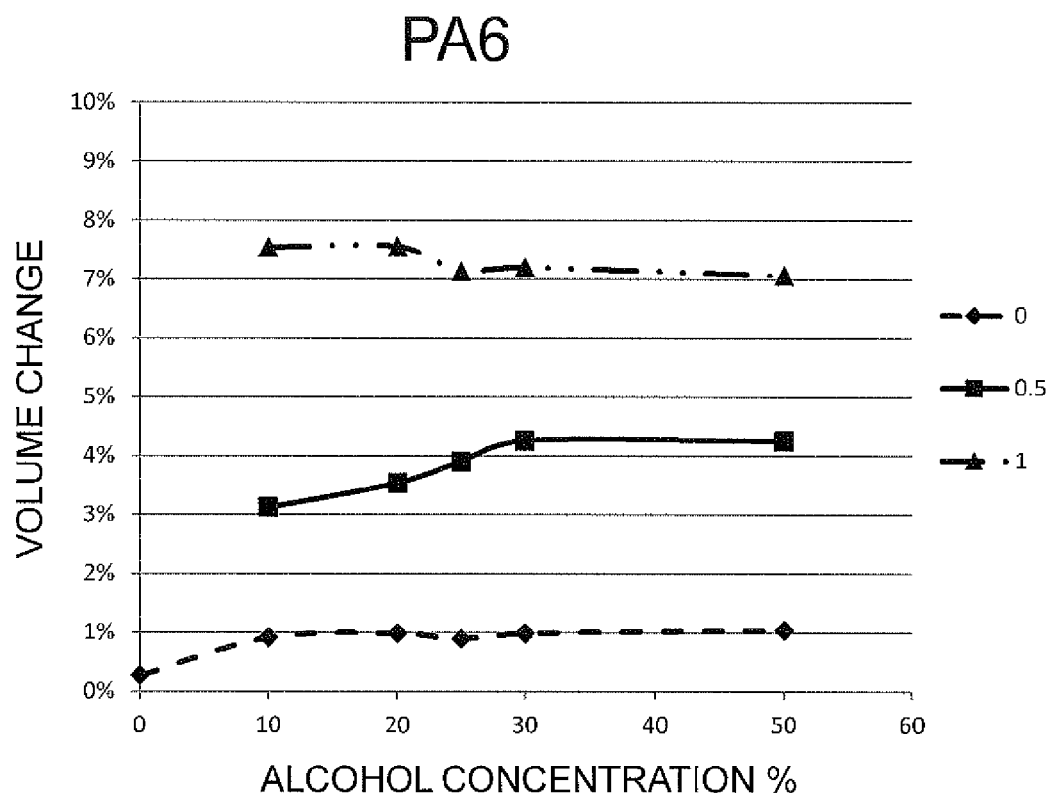
FIG. 2 is a chart representing a relationship between an alcohol concentration and a volume change ratio of a detection portion made of PA6.

FIG. 2 is a chart representing a relationship between an alcohol concentration and a volume change ratio of the detection portion 11 when the detection portion 11 made of PA6 is immersed into the alcohol containing fuel. The temperature of the alcohol containing fuel is, for example, room temperature (about 20 degrees Celsius). In FIG. 2, a dashed two-dotted line indicates a relationship between the alcohol concentration in the alcohol containing fuel and the volume change ratio of the detection portion 11 when the phase separation water ratio is 1. On the other hand, a solid line indicates a relationship between the alcohol concentration in the alcohol containing fuel and the volume change ratio of the detection portion 11 when the phase separation water ratio is 0.5. Yet on the other hand, a dashed line indicates a relationship between the alcohol concentration in the alcohol containing fuel and the volume change ratio of the detection portion 11 when the phase separation water ratio is 0, i.e., when the actual amount of water is 0. Put differently, FIG. 2 represents change value properties as a relationship between the phase separation water ratio and the volume change ratio of the detection portion 11.

FIG. 3 is a table representing a relationship among the alcohol concentration, the phase separation water ratio, and the actual amount of water. For example, when the alcohol concentration is 10% and the phase separation water ratio is 1, the actual amount of water is 0.5 volume %. In other words, when the alcohol concentration is 10%, the boundary amount of water causing the phase separation in the alcohol containing fuel is 0.5 volume %. On the other hand, when the alcohol concentration is 20% and the phase separation water ratio is 1, the actual amount of water is 1.3 volume %.

Likewise, when the alcohol concentration is 10% and the phase separation water ratio is 0.5, the actual amount of water is 0.25 volume %. On the other hand, when the alcohol concentration is 20% and the phase separation water ratio is 0.5, the actual amount of water is 0.65 volume %. Thus, even when the phase separation water ratio is constant (e.g., 0.5), the actual amount of water varies in accordance with the alcohol concentration. In other words, even when the actual amount of water is the same, the phase separation water ratio varies in accordance with the alcohol concentration.

As shown in FIG. 2, as to the detection portion 11 made of PA6, when the alcohol concentration is constant, the volume change ratio of the detection portion 11 varies in accordance with the phase separation water ratio. When described in detail, the volume change ratio of the detection portion 11 increases in accordance with an increase in the phase separation water ratio.

The output portion 12 is configured or programmed to output a signal in accordance with change of the detection portion 11. In other words, the output portion 12 is configured or programmed to output a signal in accordance with the swelling ratio of the detection portion 11. As described above, a change of the detection portion 11 includes a change in the volume of the detection portion 11, and the output portion 12 is configured or programmed to output a signal in accordance with the volume change ratio of the detection portion 11. In the present preferred embodiment, the output portion 12 includes a strain gauge. The output portion 12 is configured or programmed to convert the volume change ratio of the detection portion 11 into an electric signal and output the electric signal.

As described above, in the sensor 1 according to the present preferred embodiment, the output portion 12 is configured or programmed to output an electric signal in accordance with the volume change ratio of the detection portion 11. The volume change ratio of the detection portion 11 is associated with the phase separation water ratio. Thus, the sensor 1 according to the present preferred embodiment accurately detects the phase separation water ratio.

The detection portion 11 is preferably made of PA6 that has swelling properties, and the phase separation water ratio is detected by a change in the volume of the detection portion 11. Thus, the structure of the sensor 1 is simplified.

As shown in FIG. 2, the detection portion 11 made of PA6 includes a volume change ratio that is approximately constant regardless of the alcohol concentration when the phase separation water ratio is constant. Thus, the phase separation water ratio is accurately detected regardless of the alcohol concentration.

The detection portion 11 may not be necessarily made of PA6, and may be made of another material. For example, the detection portion 11 may be made of NBR (nitrile rubber).

Figure 4:
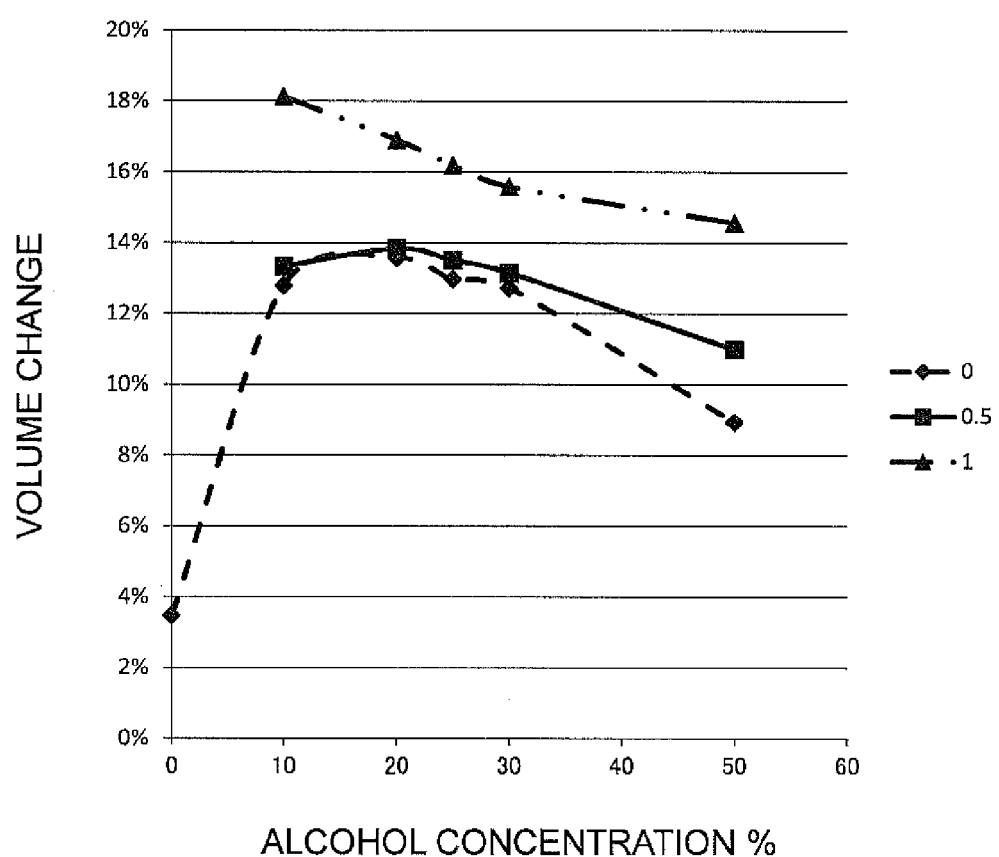
FIG. 4 is a chart representing a relationship between an alcohol concentration and a volume change ratio of a detection portion made of NBR.

FIG. 4 is a chart representing a relationship between the alcohol concentration and the volume change ratio of the detection portion 11 when the detection portion 11 made of NBR is immersed into the alcohol containing fuel. In FIG. 4, a dashed two-dotted line indicates a relationship between the alcohol concentration in the alcohol containing fuel and the volume change ratio of the detection portion 11 when the phase separation water ratio is 1. On the other hand, a solid line indicates a relationship between the alcohol concentration in the alcohol containing fuel and the volume change ratio of the detection portion 11 when the phase separation water ratio is 0.5. Yet on the other hand, a dashed line indicates a relationship between the alcohol concentration in the alcohol containing fuel and the volume change ratio of the detection portion 11 when the phase separation water ratio is 0, i.e., when the actual amount of water is 0.

As shown in FIG. 4, as to the detection portion 11 made of NBR, the volume change ratio similarly varies in accordance with the phase separation water ratio. For example, when the alcohol concentration is 10%, the volume change ratio in a phase separation water ratio of 0.5 is different from that in a phase separation water ratio of 1. This is also true with respect to the other conditions of the alcohol concentration. Therefore, the phase separation water ratio is accurately detected even when using a detection portion 11 made of NBR.

The material of which the detection portion 11 is made is not necessarily limited to the above-described PA6 or NBR as long as some factor of the material changes in accordance with the phase separation water ratio.

In the above-described preferred embodiments, the output portion 12 is configured or programmed to output a signal in accordance with a change in the volume of the detection portion 11. However, the change of the detection portion 11 is not limited to a change in volume. For example, the change of the detection portion 11 may be a change in the weight of the detection portion 11. In other words, the above-described swelling ratio is not limited to a volume change ratio and may be a weight change ratio. It should be noted that a change in weight of the detection portion 11 correlates with a change in volume of the detection portion 11. Therefore, even when the output portion 12 is configured or programmed to output a signal in accordance with a change in weight of the detection portion 11, it is possible to obtain a result similar to that obtained in FIG. 2 or 4.

Alternatively, a change of the detection portion 11 may be a change in the shape of the detection portion 11. The shape of the detection portion 11 indicates the dimensions of the detection portion 11.

The output portion 12 is not necessarily required to include the strain gauge and may include another element. For example, the output portion 12 may include a pressure sensor such as a piezoelectric element. Alternatively, the output portion 12 may include a type of switch such as a pressure switch or a limit switch, which is configured or programmed to be turned on/off in accordance with a change of the detection portion 11. Yet alternatively, another sensor that detects a change of the detection portion 11 may be provided.

The structure of the sensor 1 is not limited to that described in the above-described preferred embodiments, and may be changed. For example, the structure of the case 13 may be changed.

Figure 5:
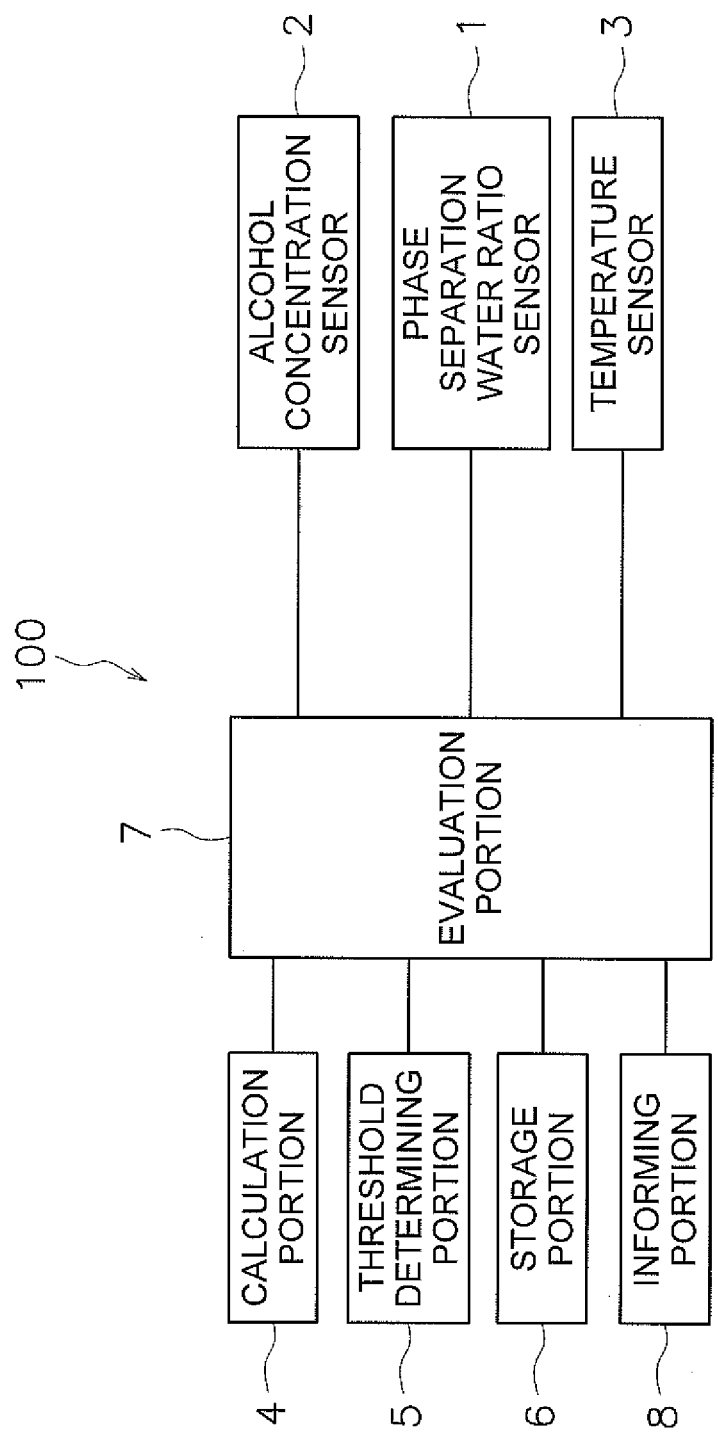
FIG. 5 is a block diagram showing a configuration of a phase separation detecting system according to a preferred embodiment of the present invention.

Next, a phase separation detecting system 100 according to a second preferred embodiment of the present invention will be explained. The phase separation detecting system 100 detects the possibility of occurrence of the phase separation in the alcohol containing fuel. FIG. 5 is a block diagram showing a configuration of the phase separation detecting system 100. As shown in FIG. 5, the phase separation detecting system 100 includes a phase separation water ratio sensor 1, an alcohol concentration sensor 2, a temperature sensor 3, a calculation portion 4, a threshold determining portion 5, a storage device 6, an evaluation portion 7, and an informing portion 8. The calculation portion 4, the threshold determining portion 5, and the evaluation portion 7 are preferably implemented by an arithmetic-and-logic unit such as a CPU, for example. The storage device 6 preferably is implemented by a memory (a RAM, a ROM, etc.) or a storage device (a HDD, a SSD, etc.), for example.

The phase separation water ratio sensor 1 is the sensor 1 according to the above-described preferred embodiments. The output portion 12 of the phase separation water ratio sensor 1 is configured or programmed to output a change value in accordance with a change of the detection portion 11 to the evaluation portion 7. The change value is an output value of a signal indicating the volume change ratio for example shown in FIG. 2 or 4. Alternatively, the change value may be an output value of a signal indicating another rate-of-change such as the weight change ratio.

The alcohol concentration sensor 2 is configured to detect the alcohol concentration in the alcohol containing fuel. The alcohol concentration sensor 2 is configured to output a detection signal indicating the detected alcohol concentration to the evaluation portion 7. The temperature sensor 3 is configured to detect the temperature of the alcohol containing fuel. The temperature sensor 3 is configured to output a detection signal indicating the detected temperature of the alcohol containing fuel to the evaluation portion 7.

The calculation portion 4 is configured or programmed to calculate a boundary amount of water based on the alcohol concentration detected by the alcohol concentration sensor 2 and the temperature of the alcohol containing fuel detected by the temperature sensor 3. For example, the storage device 6 stores information such as a table or map that defines a relationship among the alcohol concentration, the temperature of the alcohol containing fuel, and the boundary amount of water. The calculation portion 4 is configured or programmed to calculate the boundary amount of water by referring to this information.

The threshold determining portion 5 is configured or programmed to determine a threshold based on the boundary amount of water calculated by the calculation portion 4. The threshold determined by the threshold determining portion 5 is temporarily stored in the storage device 6. Further, when the boundary amount of water varies, the threshold determining portion 5 is configured or programmed to determine the threshold based on the new boundary amount of water and update the threshold stored in the storage device 6.

Figure 6:
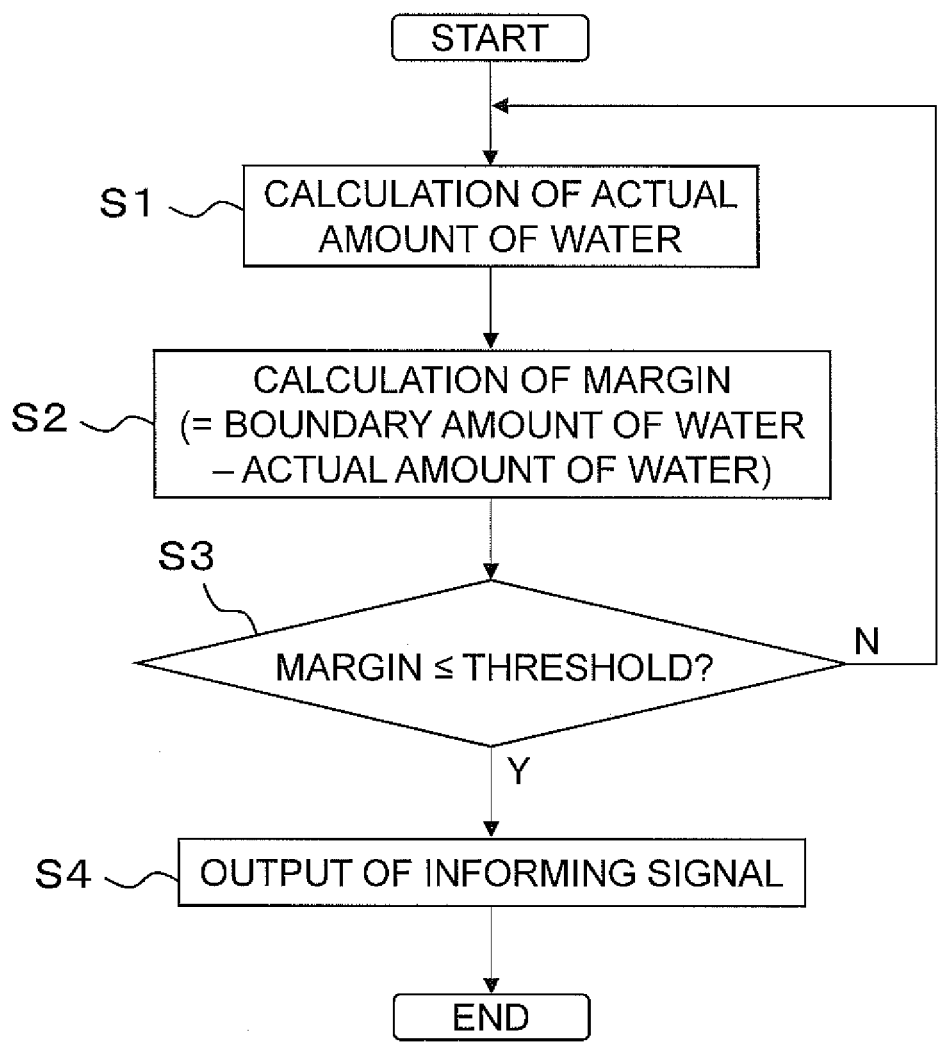
FIG. 6 is a flowchart representing a process to be performed by an evaluation portion.

The evaluation portion 7 is configured or programmed to evaluate the possibility of occurrence of the phase separation based on the threshold determined by the threshold determining portion 5 and the change value from the phase separation water ratio sensor 1. FIG. 6 is a flowchart representing a process to be performed by the evaluation portion 7.

As shown in FIG. 6, in Step S1, the evaluation portion 7 calculates the actual amount of water contained in the alcohol containing fuel. When described in detail, the evaluation portion 7 calculates the phase separation water ratio based on the change value from the phase separation water ratio sensor 1, and calculates the actual amount of water based on the phase separation water ratio and the boundary amount of water.

In Step S2, the evaluation portion 7 calculates a margin. The margin is calculated by subtracting the actual amount of water from the boundary amount of water.

In Step S3, the evaluation portion 7 determines whether or not the margin is less than or equal to the threshold. The process returns to Step S1 when the evaluation portion 7 determines that the margin is not less than or equal to the threshold. Contrarily, the process proceeds to Step S4 when the evaluation portion 7 determines that the margin is less than or equal to the threshold.

In Step S4, the evaluation portion 7 outputs an informing signal. Specifically, when it is determined that the margin is less than or equal to the threshold, the evaluation portion 7 determines that the possibility of occurrence of the phase separation is high, and outputs the informing signal.

When the evaluation portion 7 outputs the informing signal, the informing portion 8 is configured or programmed to issue a warning. For example, the informing portion 8 is a warning light, and is configured to issue a warning by lighting the warning light. It should be noted that the informing portion 8 is not limited to the warning light and may be another informing device. For example, the informing portion 8 may be a warning indication composed of characters and/or diagrams displayed on a screen. Alternatively, the informing portion 8 may be a device configured to output audio information by a buzzer or speaker.

The phase separation detecting system 100 according to the above-described preferred embodiments is configured or programmed to evaluate the possibility of occurrence of the phase separation by comparing the boundary amount of water and the actual amount of water calculated based on the change value from the phase separation water ratio sensor 1. Thus, the possibility of occurrence of the phase separation is accurately detected.

The threshold determining portion 5 is configured or programmed to determine the threshold based on the calculated boundary amount of water and update the threshold stored in the storage device 6. Therefore, the threshold is updated on a real-time basis in accordance with a variation in the boundary amount of water. The accuracy of the evaluation of the phase separation is thus enhanced.

In the above-described preferred embodiments, the evaluation portion 7 is configured or programmed to evaluate the possibility of occurrence of the phase separation by comparing the margin and the threshold. However, the method of evaluating the possibility of occurrence of the phase separation is not limited to the above. For example, the evaluation portion 7 may be configured or programmed to evaluate the possibility of occurrence of the phase separation by an evaluation method shown in FIG. 7.

Figure 7:
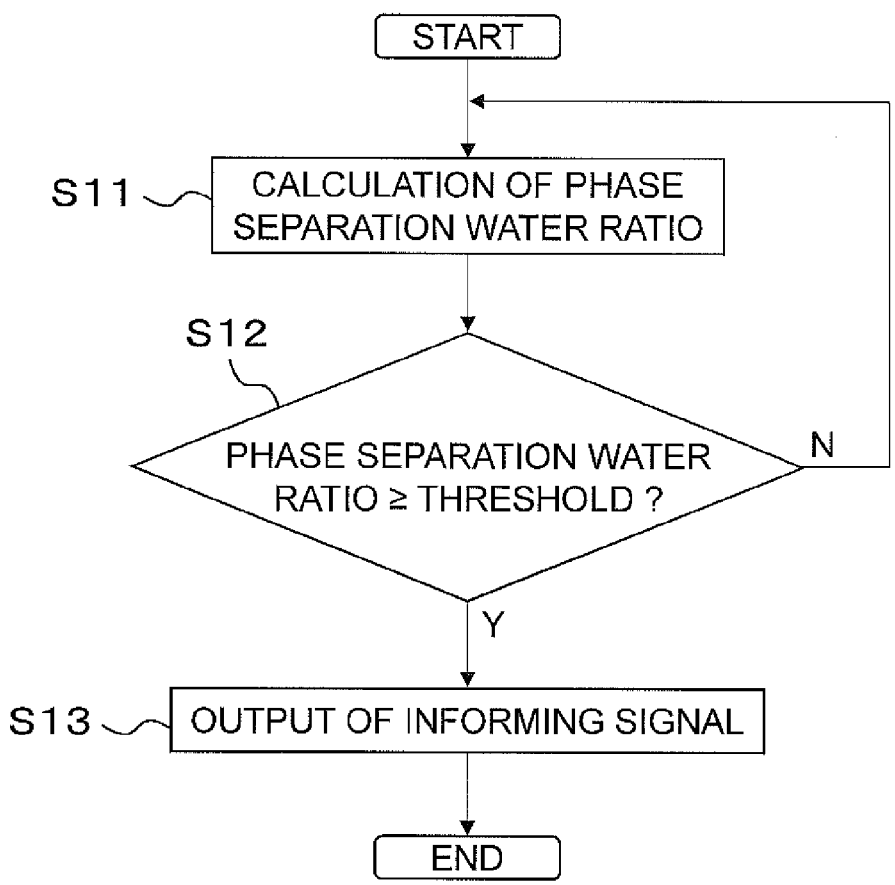
FIG. 7 is a flowchart representing a modification of the process to be performed by the evaluation portion.

As shown in FIG. 7, in Step S11, the evaluation portion 7 calculates the phase separation water ratio. When described in detail, the evaluation portion 7 calculates the phase separation water ratio based on the change value from the phase separation water ratio sensor 1 and the alcohol concentration.

In Step S12, the evaluation portion 7 determines whether or not the phase separation water ratio is greater than or equal to the threshold. The threshold is set as a ratio to the boundary amount of water. The threshold is a value of 1 or less. The threshold is preferably set to be a value of less than 1 in order to preliminarily predict the occurrence of the phase separation.

The process returns to Step S11 when the evaluation portion 7 determines that the phase separation water ratio is not greater than or equal to the threshold. Contrarily, the process proceeds to Step S13 when the evaluation portion 7 determines that the phase separation water ratio is greater than or equal to the threshold. In Step S13, the evaluation portion 7 determines that the possibility of occurrence of the phase separation is high, and outputs the informing signal. The process in Step S13 is similar to the above-described process in Step S4. Hence, detailed explanation thereof will not be hereinafter provided.

Figure 8:
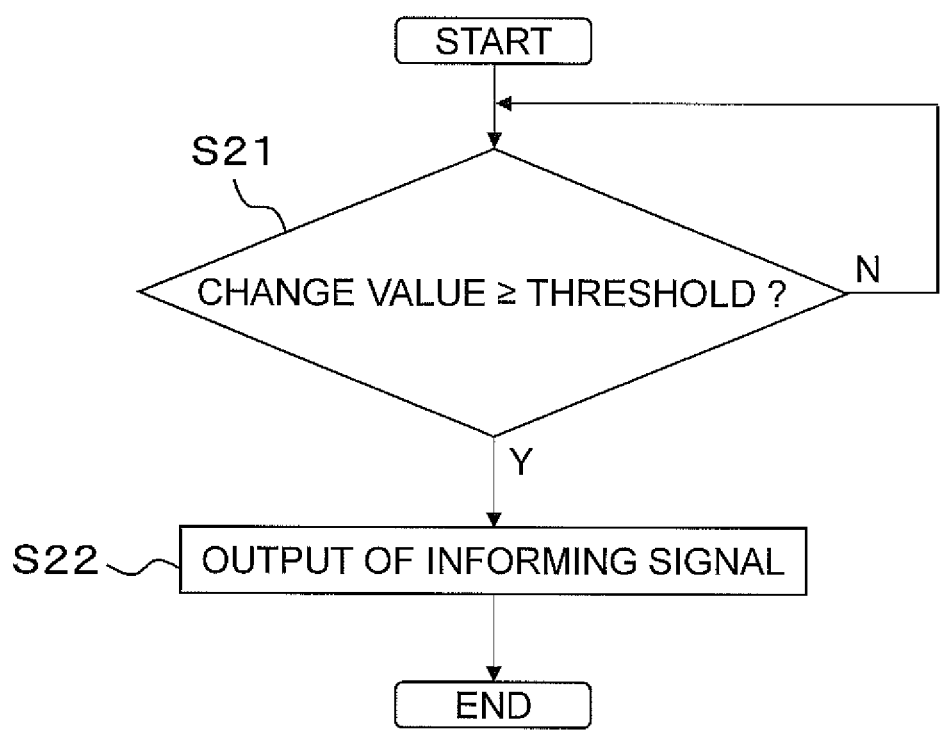
FIG. 8 is a flowchart representing another modification of the process to be performed by the evaluation portion.

Alternatively, the evaluation portion 7 may be configured or programmed to evaluate the possibility of occurrence of the phase separation by an evaluation method shown in FIG. 8. As shown in FIG. 8, in Step S21, the evaluation portion 7 determines whether or not the change value from the phase separation water ratio sensor 1 is greater than or equal to the threshold.

The evaluation process in Step S21 is repeated when the evaluation portion 7 determines that the change value from the phase separation water ratio sensor 1 is not greater than or equal to the threshold. Contrarily, the process proceeds to Step S22 when the evaluation portion 7 determines that the change value from the phase separation water ratio sensor 1 is greater than or equal to the threshold. In Step S22, the evaluation portion 7 determines that the possibility of occurrence of the phase separation is high, and outputs the informing signal. The process in Step S22 is similar to the above-described process in Step S4. Hence, detailed explanation thereof will not be hereinafter provided.

The threshold may be set in accordance with the alcohol concentration. Alternatively, when the alcohol concentration in an alcohol containing fuel to be used is set to be a constant predetermined concentration, the threshold is set in association with the predetermined concentration.

In the above-described preferred embodiments, the threshold calculated in accordance with the alcohol concentration is temporarily stored in the storage device 6. However, the threshold may be preliminarily stored in the storage device 6. For example, a single fixed value may be preliminarily stored as the threshold in the storage device 6. Alternatively, a plurality of fixed values may be preliminarily stored in the storage device 6 and a selected one of the fixed values may be used as the threshold.

The storage device 6 may preliminarily store the change value properties of the detection portion 11. The change value properties herein define a relationship between the change value and the actual amount of water. The evaluation portion 7 may be configured or programmed to calculate the actual amount of water based on the change value and the change value properties.

In the above-described preferred embodiments, the phase separation detecting system 100 preferably includes the alcohol concentration sensor 2 and the temperature sensor 3. However, either or both of the alcohol concentration sensor 2 and the temperature sensor 3 may not be provided. In this case, the possibility of occurrence of the phase separation is detected only by detecting the volume change ratio, for instance, when detection is performed only in a range as shown in FIG. 2 in which the change in volume, depending on a variation in the phase separation water ratio (the ratio of the actual amount of water to the boundary amount of water), is constant regardless of variation in the alcohol concentration.

In the above-described preferred embodiments, the phase separation detecting system 100 includes the informing portion 8. However, the informing portion 8 may not be provided. In other words, another process other than the informing process may be performed in accordance with the evaluation result by the phase separation detecting system 100.

The phase separation water ratio sensor 1 according to the above-described preferred embodiments may be used for another purpose other than detection of the possibility of occurrence of the phase separation. For example, the phase separation water ratio sensor 1 may be used for a system to prevent malfunctions from being caused by a change in the shape of a fuel-based material due to swelling, corrosion, or formation of extraneous substances due to extraction. In this case, a threshold, which could cause the above-described malfunctions, may be set for the phase separation water ratio, and the possibility of occurrence of malfunctions may be evaluated based on the threshold and the change value from the phase separation water ratio sensor 1.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

What is claimed is:

1. A sensor comprising:
   a detector made of a material that changes in accordance with a ratio of an actual amount of water to a boundary amount of water that causes a phase separation in an alcohol containing fuel, a change of the material being constant regardless of an alcohol concentration when the ratio of the actual amount of water to the boundary amount of water is constant; and
   an output device configured or programmed to output a signal in accordance with a change of the detector, the signal corresponding to the ratio of the actual amount of water to the boundary amount of water.

2. The sensor according to claim 1, wherein the change of the detector is a change in volume of the detector.

3. The sensor according to claim 1, wherein the change of the detector is a change in weight of the detector.

4. The sensor according to claim 1, wherein the change of the detector is a change in shape of the detector.

5. The sensor according to claim 1, wherein the detector is made of resin.

6. The sensor according to claim 5, wherein the detector is made of polyamide-based resin.

7. The sensor according to claim 1, wherein the output device is configured or programmed to convert the change of the detector into an electric signal and to output the electric signal.

8. The sensor according to claim 7, wherein the output device includes a strain gauge.

9. The sensor according to claim 7, wherein the output device includes a pressure sensor.

10. The sensor according to claim 7, wherein the output device includes a switch configured to be turned on/off in accordance with the change of the detector.

11. A phase separation detecting system configured to detect a possibility of occurrence of a phase separation in an alcohol containing fuel, the phase separation detecting system comprising:
   a detector made of a material that changes in accordance with a ratio of an actual amount of water to a boundary amount of water that causes the phase separation in the alcohol containing fuel, a change of the material being constant regardless of an alcohol concentration when the ratio of the actual amount of water to the boundary amount of water is constant;
   a storage configured or programmed to store a predetermined threshold;
   an output device configured or programmed to output a change value in accordance with the change of the detector, the change value corresponding to the ratio of the actual amount of water to the boundary amount of water; and
   an evaluation processor configured or programmed to evaluate the possibility of occurrence of the phase separation based on the predetermined threshold and the change value.

12. The phase separation detecting system according to claim 11, wherein the change value is a value indicating a change in volume of the detector.

13. The phase separation detecting system according to claim 11, wherein the change value is a value indicating a change in weight of the detector.

14. The phase separation detecting system according to claim 11, wherein the change value is a value indicating a change in shape of the detector.

15. The phase separation detecting system according to claim 11, wherein the detector is made of resin.

16. The phase separation detecting system according to claim 15, the detector is made of polyamide-based resin.

17. The phase separation detecting system according to claim 11, wherein the output device is configured or programmed to convert the change value into an electric signal and to output the electric signal.

18. The phase separation detecting system according to claim 17, wherein the output device includes a strain gauge.

19. The phase separation detecting system according to claim 17, wherein the output device includes a pressure sensor.

20. The phase separation detecting system according to claim 17, wherein the output device includes a switch configured to be turned on/off in accordance with the change of the detector.

21. The phase separation detecting system according to claim 11, wherein the predetermined threshold is preliminarily stored in the storage.

22. The phase separation detecting system according to claim 11, further comprising:
   an alcohol concentration sensor configured to detect an alcohol concentration of the alcohol containing fuel;
   a temperature sensor configured to detect a temperature of the alcohol containing fuel;
   a calculator configured or programmed to calculate the boundary amount of water based on the alcohol concentration detected by the alcohol concentration sensor and the temperature detected by the temperature sensor; and
   a threshold determining processor configured or programmed to determine the predetermined threshold based on the boundary amount of water calculated by the calculator.

23. The phase separation detecting system according to claim 11, wherein the evaluation processor is configured or programmed to calculate the actual amount of water contained in the alcohol containing fuel based on the change value.

24. The phase separation detecting system according to claim 23, wherein the evaluation processor is configured or programmed to evaluate the possibility of occurrence of the phase separation by comparing the calculated actual amount of water and the boundary amount of water.

25. The phase separation detecting system according to claim 23, wherein
   the predetermined threshold is a ratio to the boundary amount of water; and
   the evaluation processor is configured or programmed to calculate the ratio of the actual amount of water to the boundary mount of water based on the change value received from the output device and to evaluate the possibility of occurrence of the phase separation by comparing the calculated ratio and the predetermined threshold.

26. The phase separation detecting system according to claim 23, wherein
   the storage is configured or programmed to store preliminary change value properties of the detector; and
   the evaluation processor is configured or programmed to calculate the ratio of the actual amount of water to the boundary amount of water based on the change value and the change value properties.

27. The phase separation detecting system according to claim 11, wherein the evaluation processor is configured or programmed to evaluate the possibility of occurrence of the phase separation by comparing the predetermined threshold and the change value.

28. A phase separation detecting method of detecting a possibility of occurrence of a phase separation in an alcohol containing fuel, the method comprising the steps of:
   disposing a detector made of a material that changes in accordance with a ratio of an actual amount of water to a boundary amount of water causing the phase separation in the alcohol containing fuel, a change of the material being constant regardless of an alcohol concentration when the ratio of the actual amount of water to the boundary amount of water is constant;
   setting a predetermined threshold;
   outputting a change value in accordance with a change of the detector, the change value corresponding to the ratio of the actual amount of water to the boundary amount of water; and evaluating the possibility of occurrence of the phase separation based on the predetermined threshold and the change value.

* * * * *